(12) United States Patent
Kiga et al.

(10) Patent No.: US 7,393,670 B2
(45) Date of Patent: Jul. 1, 2008

(54) TYROSYL-TRNA SYNTHETASE VARIANTS

(75) Inventors: Daisuke Kiga, Wako (JP); Kensaku Sakamoto, Tokyo (JP); Ichiro Hirao, Asaka (JP); Shigeyuki Yokoyama, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 447 days.

(21) Appl. No.: 10/483,636

(22) PCT Filed: Jan. 11, 2002

(86) PCT No.: PCT/JP02/00118

§ 371 (c)(1),
(2), (4) Date: Jan. 13, 2004

(87) PCT Pub. No.: WO03/014354

PCT Pub. Date: Feb. 20, 2003

(65) Prior Publication Data

US 2005/0084856 A1   Apr. 21, 2005

(30) Foreign Application Priority Data

Aug. 1, 2001   (JP) .............................. 2001-234135

(51) Int. Cl.
*C12N 9/00* (2006.01)
*C07K 1/00* (2006.01)

(52) U.S. Cl. ....................... 435/183; 530/350

(58) Field of Classification Search ........................ None
See application file for complete search history.

(56) References Cited

FOREIGN PATENT DOCUMENTS

EP   1 557 469 A1   7/2005

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Ohno et al., *J. Biochem.*, vol. 130, pp. 417-423 (2001).
Hamano-Takaku et al., *J. of Biol. Chem.*, vol. 275, No. 51, pp. 40324-40328 (2000).
Bain et al., *Biochemistry*, vol. 30, pp. 5411-5421 (1991).
Barker et al., *FEBS Letters*, vol. 150, No. 2, pp. 419-423 (1982).
Winter, et al., *Eur. J. Biochem.*, vol. 132, pp. 383-387 (1983).
Brick et al., *J.Mol. Biol.*, vol. 208, pp. 83-98 (1988).
K. Sakamoto et al., "Nucleic Acids Research", vol. 30, No. 21, pp. 4692-4699 (2002).
D. Kiga et al., "Proc. of the Nat. Acad. of Sci. of USA", vol. 99, No. 15, pp. 9715-9723 (2002).
European Search Report.
Lei Wang, et al. "Expanding the Genetic Code of *Escherichia coli*" Science, vol. 292, pp. 498-500, Apr. 20, 2001.

* cited by examiner

*Primary Examiner*—Richard G Hutson
(74) *Attorney, Agent, or Firm*—Peter F. Corless; Christine C. O'Day; Edwards Angell Palmer & Dodge LLP

(57) ABSTRACT

Tyrosyl-tRNA synthetases having a modified amino acid sequence whereby unnatural amino acids can be more efficiently incorporated than original natural amino acids. More specifically, tyrosyl-tRNA synthetases having been modified at the amino acid(s) at the 37- and/or 195-positions. A method of modifying tyrosyl-tRNA synthetase characterized in that the position of an amino acid to be modified is determined based on the 3-D structure of a tyrosyl-AMP and of tyrosyl synthetase complex and an amino acid to which this enzyme binds.

2 Claims, 3 Drawing Sheets

FIG. 2

| mRNA | wt | amb | amb | amb |
|---|---|---|---|---|
| I-Tyr | + | + | + | + |
| TyrRSvariant | + | + | + | − |
| sup tRNA | + | + | − | + |
| Lane | 1 | 2 | 3 | 4 |

SEQUENCE LISTING

<160> NUMBER OF SEQ ID NOS: 14

<210> SEQ ID NO 1
<211> LENGTH: 424
<212> TYPE: PRT
<213> ORGANISM: Escherichia coli

<400> SEQUENCE: 1

Met Ala Ser Ser Asn Leu Ile Lys Gln Leu Gln Glu Arg Gly Leu Val
 1               5                  10                  15

Ala Gln Val Thr Asp Glu Glu Ala Leu Ala Glu Arg Leu Ala Gln Gly
            20                  25                  30

Pro Ile Ala Leu Tyr Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Asp Phe Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu

-continued

```
                275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
                340                 345                 350

Met Glu Lys Gly Ala Asp Leu Met Gln Ala Leu Val Asp Ser Glu Leu
            355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420

<210> SEQ ID NO 2
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggaattccat atggcaagca gtaacttgat taaacaattg caag                       44

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gccgaagctt gtcgactttc cagcaaatca gacagtaatt cttttttaccg               50

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aggatcgaag ccgcaagcga gcgcgatcgg gccttgcgcc                            40

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (17)..(18)
```

<223> OTHER INFORMATION: a, c, g or t

<400> SEQUENCE: 5
aggatcgaag ccgcamnnga gcgcgatcgg gccttgcgcc                          40

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acggtgtggt gctgtctatt ggtggttctg acc                                33

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acggtgtggt gctggcaatt ggtggttctg acc                                33

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
acggtgtggt gctgaacatt ggtggttctg acc                                33

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acggtgtggt gctgtgcatt ggtggttctg acc                                33

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttcttcggat ccaaccagac tgcgccgcct tc                                 32

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gatcatctgg ttaacggaga agtgtttgcc                                              30

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gaccttcctg cgcgatattg gcaaac                                                  26

<210> SEQ ID NO 13
<211> LENGTH: 185
<212> TYPE: PRT
<213> ORGANISM: Artificial Sequence
<220> FEATURE:
<223> OTHER INFORMATION: Description of Artificial Sequence: Synthetic
      modification of human protein

<400> SEQUENCE: 13

Met Thr Glu Tyr Lys Leu Val Val Val Gly Ala Gly Gly Val Gly Lys
 1               5                  10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gly Gly Val Glu Asp Ala Phe Tyr Thr Leu Val
145                 150                 155                 160

Arg Glu Ile Arg Gln His Lys Leu Arg Lys Leu Gly Ser Leu Val Pro
                165                 170                 175

Arg Gly Ser His His His His His His
            180                 185

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      amino acid sequence
<220> FEATURE:
<221> NAME/KEY: MOD_RES
<222> LOCATION: (5)
<223> OTHER INFORMATION: (iodo-Tyr)

-continued

<400> SEQUENCE: 14

Phe Val Asp Glu Tyr Asp
 1               5

TYROSYL-TRNA SYNTHETASE VARIANTS

TECHNICAL FIELD

The present invention relates to tyrosyl-tRNA synthetase of which amino acid sequence is modified whereby capable of incorporating unnatural tyrosine analogue substituted at position 3 more efficiently than original natural tyrosine by modifying the amino acid sequence of the tyrosyl-tRNA synthetase, and preferably to tyrosyl-tRNA synthetase variants where two or more amino acids are modified. The tyrosyl-tRNA synthetase of the invention of which amino acid sequence is modified can incorporate unnatural tyrosine analogue substituted at position 3, e.g., 3-iodo-tyrosine more efficiently than original natural tyrosine, and more intensively utilize it than tyrosine which is a substrate of wild-type of tyrosyl-tRNA synthetase. Therefore, the use thereof can produce proteins (alloproteins) containing unnatural amino acids selectively and site-specifically at a high efficiency.

BACKGROUND ART

Variant proteins have been produced where a certain amino acid residue of a protein is substituted with an amino acid other than 20 canonical amino acids (referred to as an unnatural amino acid hereinafter) involved in typical protein synthesis. It has been advocated that the protein which contains unnatural amino acids is referred to as the alloprotein (Koide et al., Proc. Natl. Acad. Sci. USA, 85:6237-41, 1988). It makes finer and systematic modification possible that the certain residue can be also replaced by the unnatural amino acid, compared to the cases where the replacements occur among 20 types of natural amino acids. Also, the amino acid with characteristic fluorescent property, the amino acid of which structure can be optically controlled, the amino acid with a reaction group applicable as a optic crosslinker, and the like have been introduced into the proteins.

There are some techniques to produce the alloproteins. Koide et al. made *Escherichia coli* incorporate an unnatural amino acid added to medium, which was used instead of one certain type of the canonical amino acids to produce the alloprotein. However, only 20 types together with canonical amino acids and unnatural amino acids can be used in this technique (Koide et al., Proc. Natl. Acad. Sci. USA, 85:6237-41, 1988).

Alternatively, the alloprotein is produced by adding the suppressor tRNA which has been aminoacylated beforehand in a separate system to a cell-free translation system (Noren et al., Science, 244:182-8, 1989). The disadvantage of this method includes a necessity to prepare aminoacyl-tRNA in a large amount.

In order to prepare the protein comprising 21 types of amino acids including the unnatural amino acid in the larger amount, it is necessary to construct an artificial genetic code system in which the tRNA attaching the unnatural amino acid is aminoacylated by its cognate aminoacyl-tRNA synthetase (aaRS) in the system where the translation reaction is conducted. The aminoacyl-tRNA synthetase is an enzyme which specifically attaches the amino acid to the tRNA, and 20 types occur corresponding to respective 20 types of canonical amino acids for each biological species excluding some exceptions. In a cell, these enzymes determine the type of the amino acid assigned to the genetic code where basically one type of such an aaRS exists for every amino acid. For instance, tyrosyl-tRNA synthetase (TyrRS) which is one of aminoacyl-tRNA synthetase (aaRS) discriminates tRNA for tyrosine from the other tRNA for the other amino acids, and makes it attach to only tyrosine but not the other amino acids.

In the meanwhile, Wang et al. expressed TyrRS variants derived from *Methanococcus janasii* modified so as to attach O-methyltyrosine specifically and amber suppressor tRNA engineered by the modification of tyrosine tRNA derived from the same organism, in *E. coli* (Wang et al., Science, 292:498-500, 2001). This TyrRS and tyrosine tRNA from *Methanococcus janasii* do not react with tRNA and aaRS from *E. coli*, respectively. Thus, it has been reported that O-methyltyrosine is incorporated specifically corresponding to an amber codon in this study.

In order to construct such an artificial genetic code system, it is critical that a pair of aaRS and tRNA which does not react with aaRS from the host is found and that the aaRS variant which reacts specifically with the unnatural amino acid is developed. As the aaRS which reacts specifically with the unnatural amino acid, only TyrRS modification specific for O-methyltyrosine mentioned above has been known so far.

As tyrosine analogues substituted at position 3, there are DOPA involved in intercellular signal transduction, 3-iodotyrosine capable of becoming a target site of site-specific labeling in the protein, and the like. These have been known as the unnatural amino acids which exert physiological activity. Therefore, it is desired to obtain TyrRS specific for the tyrosine analogues substituted at position 3. No TyrRS variant has been known so far, which incorporates such tyrosine analogues substituted at position 3 more efficiently than tyrosine. The TyrRS variant was reported at an academic meeting, which incorporates the tyrosine analogues substituted at position 3 more efficiently than the wild-type TyrRS. However, since this variant incorporates tyrosine and the tyrosine analogue at a similar efficiency, it is inappropriate for inserting only the unnatural amino acid in the certain site of the protein.

DISCLOSURE OF THE INVENTION

The present invention provides a novel tyrosyl-tRNA synthetase variant which can incorporate preferentially an unnatural amino acid, more particularly tyrosine analogue having the substitution at position 3 of phenyl group of the tyrosine. More particularly, provided is a novel tyrosyl-tRNA synthetase variant wherein the unnatural amino acid is 3-halotyrosine such as 3-iodotyrosine.

Also, the invention provides a novel method for producing protein containing the unnatural amino acid (alloprotein) by a protein production system using the novel tyrosyl-tRNA synthetases which can preferentially incorporate the unnatural tyrosine analogue substituted at position 3.

Further, the invention provides a method for designing the tyrosyl-tRNA synthetases which can preferentially and efficiently incorporate the unnatural tyrosine analogues substituted at position 3, and cells transformed by a gene encoding the tyrosyl-tRNA synthetase designed in such a method and production of the proteins containing the unnatural amino acid in the cells, as well as a production means of the proteins including the unnatural amino acid in a cell-free translation system to which the designed aminoacyl-tRNA synthetase is added.

BRIEF DESCRIPTION OF THE DRAWINGS

FIG. 2 shows amber suppression in a wheat germ cell-free translation system. Translation products labeled with $^{14}$C-leucine were analyzed by SDS-PAGE. The amber suppression was observed only when both TyrRS-VC variant and suppressor tRNA were present. A symbol, amb is mRNA in which the 32nd codon was replaced by the amber codon, and sup tRNA is the amber suppressor tRNA derived from tRNA$^{Tyr}$ from E. coli.

Figure 1:
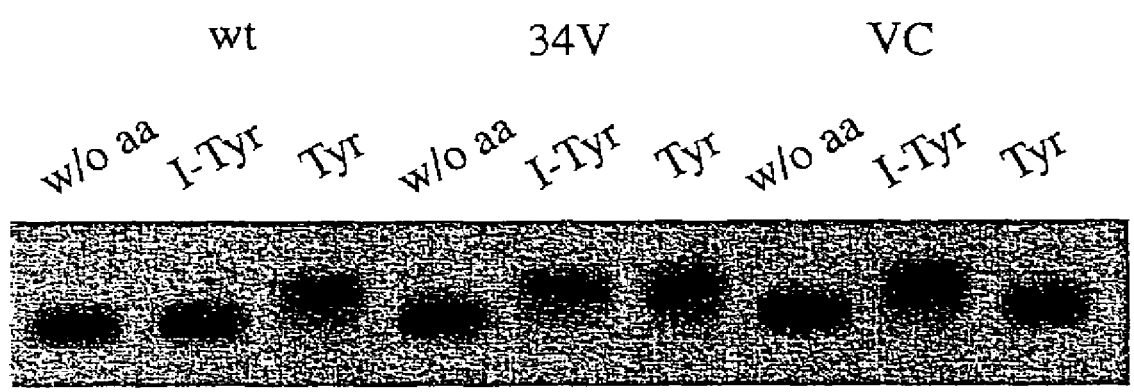
FIG. 1 is a photo, substitute for a drawing, showing the results of aminoacylation activity where the aminoacyl-tRNA synthetase variants of the invention were assayed by the same method as acidic polyacrylamide gel electrophoresis.

K3 and K9 are lysylendopeptidase digested fragments of Ras protein, respectively. They were found to be Ser 17-Lys 42 fragment and Thr 148-Lys 167 fragment by mass spectrometry. The upper and lower panels show the analysis of the translation products of mRNA comprising no amber codon and mRNA in which 32nd codon is the amber codon, respectively. A fragment (K3-IY32) having a mass corresponding to the fragment where one tyrosine residue of the K3 fragment was replaced by iodotyrosine was found in the analysis of the product of the amber suppression (lower panel).

BEST MODE FOR CARRYING OUT THE INVENTION

The present invention relates to tyrosyl-tRNA synthetases having a modified amino acid sequences whereby capable of incorporating unnatural tyrosine analogues substituted at position 3 more efficiently than an original natural tyrosine. More particularly, the invention relates to the tyrosyl-tRNA synthetases capable of incorporating amino acids substituted at position 3 of tyrosine which are unnatural type of amino acids efficiently and selectively, by modifying two or more sites of amino acids of the amino acid sequence of the tyrosyl-tRNA synthetase at residues presumed to recognize the target tyrosine with the other amino acids on the basis of its tertiary structure.

Also, the invention relates to a method for modifying the amino acid sequence of the tyrosyl-tRNA synthetase. This modification is characterized in that amino acids at the site where the tyrosyl-tRNA synthetase binds to tyrosine or tyrosyl-AMP are determined on the basis of its three dimensional structure and the amino acids are modified with the other amino acids, preferably two or more amino acids are modified with the other amino acids, when producing the tyrosyl-tRNA synthetase having the modified amino acid sequence whereby capable of incorporating the unnatural tyrosine analogue substituted at position 3 more efficiently than the original natural tyrosine by modifying the amino acid sequence of the tyrosyl-tRNA synthetase.

Further, the invention relates to a method for producing proteins containing the unnatural amino acids using the tyrosyl-tRNA synthetases having the modified amino acid sequence of the invention. More particularly, the invention relates to a method for producing the proteins containing the tyrosine analogues substituted at position 3 of tyrosine which are the unnatural type amino acids using the tyrosyl-tRNA synthetases having the modified amino acid sequence.

Also, the invention relates to cells transformed by a gene encoding such a tyrosyl-tRNA synthetase having the modified amino acid sequence, and production of proteins comprising the unnatural amino acids in such cells as well as a production means of the proteins comprising the unnatural amino acids in a cell-free translation system to which the designed aminoacyl-tRNA synthetase is added.

The present inventors have studied on methods capable of producing alloproteins efficiently, selectively and in a large scale, and developed the aminoacyl-tRNA synthetases capable of incorporating the unnatural type amino acid preferentially and efficiently therefor. Tyrosyl-tRNA synthetase (TyrRS) is one type of the aminoacyl-tRNA synthetases, and the present inventors focused on the tyrosine analogue recognizing tyrosyl-tRNA synthetase (TyrRS) variants which recognize tyrosine analogues since the tyrosine analogues substituted at position 3 per se have various types of physiological activity. Also, it has been known that TyrRS and tyrosine tRNA derived from E. coli do not react with tyrosine tRNA and TyrRS from eukaryotic organisms, respectively. Thus, a TyrRS variant specific for the tyrosine analogues substituted at position 3 is also promising as a material to construct an artificial genetic code system for the site-specific incorporation of the unnatural amino acid into a protein.

Therefore, the following illustration is carried out citing the tyrosyl-tRNA synthetase (TyrRS) as a specific example of the aminoacyl-tRNA synthetases.

The present inventors studied on the improvement of the amino acids at a substrate binding site of the enzyme to obtain TyrRS variants specific for the tyrosine analogues substituted at position 3. The amino acid sequence of TyrRS derived from E. coli has been already known and it is shown at the sequence No.1 in the sequence listing. Also the amino acid sequence is shown below using the single character code of amino acids (SEQ ID NO: 1).

| | | | |
|---|---|---|---|
| MASSNLIKQL | QERGLVAQVT | DEEALAERLA | 30 |
| QGPIALYCGF | DPTADSLHLG | HLVPLLCLKR | 60 |
| FQQAGHKPVA | LVGGATGLIG | DPSFKAAERK | 90 |
| LNTEETVQEW | VDKIRKQVAP | FLDFDCGENS | 120 |
| AIAANNYDWF | GNMNVLTFLR | DIGKHFSVNQ | 150 |
| MINKEAVKQR | LNREDQGISF | TEFSYNLLQG | 180 |
| YDFACLNKQY | GVVLQIGGSD | QWGNITSGID | 210 |
| LTRRLHQNQV | FGLTVPLITK | ADGTKFGKTE | 240 |
| GGAVWLDPKK | TSPYKFYQFW | INTADADVYR | 270 |
| FLKFFTFMSI | EEINALEEED | KNSGKAPRAQ | 300 |
| YVLAEQVTRL | VHGEEGLQAA | KRITECLFSG | 330 |
| SLSALSEADF | EQLAQDGVPM | VEMEKGADLM | 360 |
| QALVDSELQP | SRGQARKTIA | SNAITINGEK | 390 |
| QSDPEYFFKE | EDRLFGRFTL | LRRGKKNYCL | 420 |
| ICWK | | | 424 |

The present inventors studied and determined which residues on the enzyme should be replaced as follows. Three dimensional structure of Bacillus stearothermophilus TyrRS -tyrosyl-AMP complex has been already reported (Brick et al., J. Mol. Bio., 208:83, 1988), and the residues where the tyrosine analogues substituted at position 3 should be incorporated were presumed on the basis of this three dimensional structure. Although this is a relationship of the TyrRS -tyrosyl-AMP complex in Bacillus stearothermophilus, the present inventors supposed that it is possible to figure similarly for TyrRS derived from the other organisms because of highly conservative TyrRS in biological species.

Based on this three dimensional structure model, the present inventors found the amino acids at positions 37 and 195 as the residues where the replacements should be introduced into TyrRS of *E. coli* so as to incorporate the tyrosine analogues substituted at position 3. The amino acid at position 37 is tyrosine (Y) and the amino acid at position 195 is glutamine (Q) in the wild-type TyrRS. They are the underlined positions in the amino acid sequence described above.

First, an expression vector, pET-YRS for TyrRS was made by preparation of the fragment amplified by PCR using the following primers (1) and (2) and using a plasmid including TyrRS gene of *E. coil* as a template, and digestion of the fragment with NdeI and HinIII, followed by the insertion into a NdeI-HinIII site of pET26b.

```
Primer (1):                      (SEQ ID NO: 2)
5'-GGAATTCCATATGGCAAGCAGTAACTTGATTAAACAATT
GCAAG-3'

Primer (2):                      (SEQ ID NO: 3)
5'-GCCGAAGCTTGTCGACTTTCCAGCAAATCAGACAGTAATTCT
TTTTACCG-3
```

Next, the method for the site-directed mutagenesis of the amino acids at the residues 37 and/or 195 is illustrated.

First, a single amino acid substitution was made where the amino acid at either position of 37 or 195 was substituted. The primers (3) to (8) used for making the DNA sequences encoding the substitutions of one amino acid at positions 37 and 195 are shown below.

```
Primer (3):                      (SEQ ID NO: 4)
5'-AGGATCGAAGCCGCAAGCGAGCGCGATCGGGCCTTGCGCC-3'

Primer (4):                      (SEQ ID NO: 5)
5'-AGGATCGAAGCCGCAMNNGAGCGCGATCGGGCCTTGCGCC-3'
M denotes C or A, and
N denotes A,C,G or T.
```

M denotes C or A, and N denotes A, C, G or T.

```
                                 (SEQ ID NO: 6)
Primer (5): 5'-ACGGTGTGGTGCTGTCTATTGGTGGTTCTGACC-3'

(SEQ ID NO: 7)
Primer (6): 5'-ACGGTGTGGTGCTGGCAATTGGTGGTTCTGACC-3'

(SEQ ID NO: 8)
Primer (7): 5'-ACGGTGTGGTGCTGAACATTGGTGGTTCTGACC-3'

(SEQ ID NO: 9)
Primer (8): 5'-ACGGTGTGGTGCTGTGCATTGGTGGTTCTGACC-3'
```

Next, a double amino acid substitution was made where both amino acids at the position 37 and 195 were modified.

The DNA sequence encoding the double amino acid substitution was made by an overlap extension method using the primers from the plasmids encoding the respective single amino acid substitutions at the residues 37 and 195 made in the above step, and inserted into an NdeI-BamHI site of pET-YRS. The overlap extension method was carried out by purifying two fragments obtained by the amplification using a pair of the primers (1) and (10) and a pair of the primers (9) and (11), and subsequently amplifying by PCR using the primers (1) and (9) therewith.

```
Primer (1):                      (SEQ ID NO: 2)
5'-GAATTCCATATGGCAAGCAGTAACTTGATTAAACAATT
GCAAG-3'

Primer (10):                     (SEQ ID NO: 11)
5'-GATCATCTGGTTAACGGAGAAGTGTTTGCC-3'

Primer (9):                      (SEQ ID NO: 10)
5'-TTCTTCGGATCCAACCAGACTGCGCCGCCTTC-3'

Primer (11):                     (SEQ ID NO: 12)
5'-GACCTTCCTGCGCGATATTGGCAAAC-3'
```

Modifications of the amino acids obtained in this way and their symbols are shown in the following Table 1.

TABLE 1

| Symbols of wild-types and modifications of amino acids and types of amino acids | | |
|---|---|---|
| Symbol | Position 37 | Position 195 |
| Wild-type | Tyrosine (Y) | Glutamine (Q) |
| 37A | Alanine (A) | Glutamine (Q) |
| 37V | Valine (V) | Glutamine (Q) |
| 37I | Isoleucine (I) | Glutamine (Q) |
| 37L | Leucine (L) | Glutamine (Q) |
| 195S | Tyrosine (Y) | Serine (S) |
| 195C | Tyrosine (Y) | Cysteine (C) |
| 195N | Tyrosine (Y) | Asparagine (N) |
| 195A | Tyrosine (Y) | Alanine (A) |
| AS | Alanine (A) | Serine (S) |
| VS | Valine (V) | Serine (S) |
| IS | Isoleucine (I) | Serine (S) |
| LS | Leucine (L) | Serine (S) |
| AC | Alanine (A) | Cysteine (C) |
| VC | Valine (V) | Cysteine (C) |
| IC | Isoleucine (I) | Cysteine (C) |
| LC | Leucine (L) | Cysteine (C) |
| AN | Alanine (A) | Asparagine (N) |
| VN | Valine (V) | Asparagine (N) |
| IN | Isoleucine (I) | Asparagine (N) |
| LN | Leucine (L) | Asparagine (N) |
| AA | Alanine (A) | Alanine (A) |
| VA | Valine (V) | Alanine (A) |
| IA | Isoleucine (I) | Alanine (A) |
| LA | Leucine (L) | Alanine (A) |

Each complete variant DNA fragment obtained at the above step was inserted into an original position in the plasmid pETYRS. *E. coli* BLR(DE3) was transformed with the plasmid including the wild-type and variant-type tyrS genes by the transformation method according to Hanahan's method (Hanahan, D., J. Mol. Bio., 166:557-580). The wild-type and variant-type TyrRS were expressed by isolating and culturing the transformants having respective plasmids. The wild-type and variant-type TyrRS proteins were purified from the *E. coli* crude extracts.

Assays of substrate specificity were carried out for the resultant modifications. The following three assay methods were used for the assays.

In the first method, Lloyd's method (Nucleic Acids Research, 23:2886-2892, 1995) where inorganic phosphate produced by pyrophosphatase-drived hydrolysis of pyrophosphate which was one of the reaction products of the aminoacylation reactions was quantified was simplified, and the inorganic phosphate was detected using Biomol green (Funakoshi) to carry out the measurement of the aminoacylation reaction. The results are shown in Tables 2 and 3.

In the second method, Lloyd's method (Nucleic Acids Research, 23:2886-2892, 1995) was carried out without alteration. The results are shown in Table 4.

In the third method, levels of aminoacylation activity in the presence of tyrosine or 3-iodotyrosine for the full-length tRNA were assayed by the same method as. acidic polyacrylamide gel electrophoresis described by Wolfson et al. (Wolfson, A. D. et al., RNA, 4:1019-1023, 1998). The result is shown in FIG. 1 as a photo, substitute for a drawing.

TABLE 2

Aminoacylation activity of wild-type and single amino acid variant enzymes

|  | Tyrosine | 3-Iodotyrosine |
|---|---|---|
| Wild-type | *** | — |
| 37A | *** | *** |
| 37V | *** | *** |
| 37I | ** | *** |
| 37L | *** | *** |
| 195S | *** | * |
| 195C | *** | * |
| 195N | *** | * |
| 195A | *** | * |

Marks in the table denote that the activity is high in the order of * >  > * > —.

Each mark shows that the aminoacylation reaction was detected by a microplate reader in the reaction at enzyme concentrations of 50 nM, 500 nM and 5 μM at 37° C. for 4 min. Amino acid concentrations were 200 μM and 1 mM for tyrosine and 3-iodotyrosine, respectively.

TABLE 3

Aminoacylation activity of wild-type, 37V and double variant enzymes

|  | Tyrosine | 3-iodotyrosine |
|---|---|---|
| Wild-type | *** | — |
| 37V | *** | *** |
| AS | * | * |
| VS | ** | ** |
| IS | — | — |
| LS | — | — |
| AC | * | ** |
| VC | * | ** |
| IC | — | — |
| LC | * | * |
| AN | — | — |
| VN | — | ** |
| IN | — | — |
| LN | * | — |
| AA | — | — |
| VA | * | ** |
| IA | * | * |
| LA | * | — |

Marks in the table denote that the activity is high in the order of * >  > * > —.

Each mark shows that the reaction could be detected strongly at 25 nM, strongly at 250 nM and weakly at 250 nM of enzyme concentrations in the aminoacylation reaction at 37° C. for 4 min. Amino acid concentrations were 200 μM and 1 mM for tyrosine and 3-iodotyrosine, respectively.

Table 2 lists the levels of aminoacylation activity of the wild-type enzyme and 8 variant enzymes with a single amino acid mutation, and Table 3 lists the levels of aminoacylation activity of the wild-type, 37V enzymes and 16 variant enzymes with double mutations. Concerning the enzyme variants obtained by substitutions of Tyr 37 and Gln 195 with the other amino acids, the levels of aminoacylation activity were substantially increased against the tyrosine analogue substituted at position 3 (3-iodotyrosine in this experiment). On the other hand, relatively, the levels of aminoacylation activity of these proteins specific for tyrosine are decreased. Therefore, the enzyme variants with relatively higher ratio of tyrosine analogue to tyrosine than that of the wild-type emerged.

TABLE 4

Aminoacylation activity of enzymes with double mutations
Initial velocity of release of pyrophosphates
(nM PPi/min/nM enzyme) at 37° C.

|  | Tyrosine | 3-iodotyrosine |
|---|---|---|
| Wild-type | 400 | <0.05 |
| 37V | 140 | 73 |
| 37A | 51 | 12 |
| AC | 1.0 | 3.1 |
| VC | 0.9 | 9.5 |
| VS | 19 | 18 |
| VN | 2.1 | 6.9 |
| VA | 3.7 | 6.6 |

Table 4 lists the levels of aminoacylation activity of the enzymes with double mutations determined by Lloyd's method described in Nucleic Acids Research, 23:2886-2892, 1995. Four enzymes with double mutations combine the advantage of variants at both Tyr 37 and Gln 195. For instance, the relative tyrosine analogue to tyrosine ratio of VC is more than 10, and the ratio of VC is higher than that of 37V, the enzyme with a single mutation, due to further introduction of the replacement at Gln 195. VN, VS and AC are inferior to VC in the relative tyrosine analogue to tyrosine ratio, but have the higher relative tyrosine analogue to tyrosine ratio than those of the substitution with a single amino acid.

Also from the result shown in Table 4, it was concluded that the combination of the variants at positions 37 and 195 dramatically altered the substrate specificity of the enzyme and that the level of aminoacylation activity for the tyrosine analogue substituted at position 3 could be increased. It is also found that VC, VN and AC have the most notable property and applicability among the enzyme variants.

FIG. 1 is a photo, substitute for a drawing, showing the aminoacylation activity of the enzymes with double mutations. The assay was carried out for the VC having the highest tyrosine analogue to tyrosine ratio by acidic PAGE where an actual attachment of an amino acid to tRNA could be examined. As a result, it was found that VC had a high specificity for the tyrosine analogue.

Production of the protein containing iodotyrosine was attempted by the reaction by a batch method in a wheat germ cell-free protein synthesis system using the resultant VC and an amber suppressor tRNA derived from tyrosine tRNA of *E. coli*. A short chain type of c-H-Ras added His-tag at the C-terminus via a spacer sequence (Milburn et al., Science 247:939-45, 1990) was used as the target protein. In translation where the template was mRNA made from a construction where the 32nd codon of this protein was replaced by the amber codon, the production of the protein in full length was dependent on coexistence of both TyrRS and the suppressor tRNA (FIG. 2). This proves that the suppressor tRNA used is scarcely aminoacylated by the endogenous aminoacyl-tRNA synthetase in the wheat germs. A synthetic quantity by the amber suppression was 30 to 40% of that of a control with no amber codon. In order to increase the synthetic quantity of the protein, the reaction by the suppression was carried out for 3 days using a dialysis method. In this case, it was found that the quantity of the production was 0.1 mg or more in terms of the quantity per ml of reaction solution and that the protein could be synthesized sufficiently in quantity to perform various experiments using proteins.

It was examined by mass spectrometry that iodotyrosine was actually inserted at the position corresponding to the amber codon of the peptide chain. Ras protein purified using nickel beads was applied on SDS-PAGE. A band corresponding to a mobility of Ras among stained product bands was cut out and treated with peptidase. A resultant fragment was analyzed by LC-MS (liquid chromatography—mass spectrometry). The 32nd codon of Ras protein used as a reporter protein is the codon for tyrosine. For mRNA where this codon was modified with the amber codon and for intact mRNA, the translation reaction was carried out where iodotyrosine, VC variant and the suppressor tRNA were all added to the translation system in the reaction solution. Among the fragments obtained by digesting the translation products, the fragment including the 32nd amino acid from N-terminus (Ser 17 to Lys 42, referred to as K3 fragment) was focused and analyzed. As a result, the majority of the K3 fragments produced by the amber suppression had the mass corresponding one where one residue of tyrosine was replaced by iodotyrosine, and K3 fragments not including iodotyrosine was minor. No K3 fragment was detected where the other amino acid was accidentally inserted at the site corresponding to the amber codon. The ratio of iodotyrosine to tyrosine inserted to the amber codon was examined by absorbance of chromatogram. Consequently, it was found that 95% or more of K3 fragments encompassed iodotyrosine by the amber suppression whereas the ratio of tyrosine insertion at the amber codon was 5% or less. On the other hand, no fragment having the mass corresponding to the case encompassing iodotyrosine in place of tyrosine was detected in the analysis of the translation products from mRNA which contained no amber codon. This confirmed that the canonical codon for tyrosine was not contaminated with iodotyrosine.

The method of the invention was illustrated by the use of Ras protein as an example, but it is obvious that the method of the invention is not limited to Ras protein and can be similarly applied for the other proteins.

As described above, the tyrosyl-tRNA synthetase was illustrated by citing TyrRS of E. coli as the specific example. It has been shown by the specific example that various enzyme variants having tyrosylation activity where the relative ratio of the unnatural amino acid, tyrosine analogue substituted at position 3 to tyrosine, is high can be found by converting tyrosine at position 37 and glutamine at position 195 to the other amino acids in the wild-type TyrRS of E. coli. Also, such enzyme variants made it possible to apply for the production of the protein with site-specific incorporation of the tyrosine analogue substituted at position 3.

Moreover, it is obvious that the method of the invention can be widely applied for the modification of tyrosyl-tRNA synthetases in other biological species since the amino acid residues at positions 37 and 195 in the wild-type TyrRS of E. coli used here are highly conserved in biological species.

The translation system utilized here is the wheat germ cell-free translation system, but it is obvious that the unnatural amino acid can be introduced site-specifically by the use of the VC variant made in the invention similarly in the cell-free translation systems of the other eukaryotic organisms and in eukaryotic cells. Also, the protein where all tyrosine residues are replaced by the unnatural amino acid can be made in a prokaryotic translation system by the use of this enzyme. The generation of such a protein also becomes possible by modifying the tyrosyl-tRNA synthetase derived from the other prokaryotic organisms as with the invention. On the other hand, it becomes possible to generate proteins containing the unnatural amino acids site-specifically in the prokaryotic translation systems by modifying the tyrosyl-tRNA synthetase derived from an eukaryotic organism or archaebacteria as with the invention.

The present invention is aimed to provide the enzyme variants in which the substrate specificity of the tyrosyl-tRNA synthetase is altered. More particularly, the invention is characterized in that the variant of tyrosyl-tRNA synthetase capable of producing the alloprotein in a large quantity containing the unnatural amino acid efficiently and selectively is prepared by modifying the amino acid sequence of the tyrosyl-tRNA synthetase.

The tyrosyl-tRNA synthetase of the invention is characterized by being capable of selectively, preferentially, and efficiently incorporating a tyrosine analogue substituted at position 3 such as 3-halotyrosine such as 3-iodotyrosine, and 3-hydroxytyrosine known to have various physiological activities as the unnatural amino acid. Also, the tyrosyl-tRNA synthetase of the invention may be those derived from any organisms such as bacteria such as E. coli, yeast, animals and plants, but it is preferable that enzymes with known three dimensional structure and those which are highly conservative as described previously are widely used. Also, even if the tyrosyl-tRNA synthetase is specific for the certain organism, if its variant is not harmful for another organism, it acts in the organism as the tyrosyl-tRNA synthetase for the new amino acid, and thus it can be used as the preferable variant.

As the method to determine the position where the amino acid sequence of the tyrosyl-tRNA synthetase of the invention is modified, it is preferable to determine the position of the amino acid to be modified on the basis of three dimensional structures of the tyrosyl-tRNA synthetase and the enzyme-bound amino acid or AMP complex of the amino acid (aminoacyl-AMP and aminoacyl-AMP analogues), but the method is not limited thereto. On the basis of the case of the tyrosyl-tRNA synthetase exemplified above where the amino acids were at the residues 37 and 195, the position of amino acid to be modified can be determined at the corresponding site in the Rossman fold domain of the other class I aminoacyl-tRNA synthetases or in the anti-parallel i-sheet domain of the class II aminoacyl-tRNA synthetases.

In the invention, it is preferable to choose two or more amino acid residues as the positions to be modified, whereby having been capable of remarkably improving the selectivity for the unnatural amino acid.

When the positions of amino acid to be modified are determined on the basis of the three dimensional structure, the positions of amino acid to be modified can be determined by first analyzing the tertiary structure of aminoacyl-tRNA synthetase of the target amino acid and subsequently analyzing the positions to which the AMP complex of the target amino acid is bound in that tertiary structure.

Also, in the above example, the modified positions included the residues 37 and 195 because the tyrosyl-tRNA synthetase derived from E. coli was used. However, this is the case of E. coli. When the tyrosyl-tRNA synthetase derived from another organism is used, the amino acids corresponding to the residues 37 and 195 of tyrosyl-tRNA synthetase derived from E. coli in the tertiary structure are the positions to be modified. In the invention, "corresponding position in the three dimensional structure" indicates the position of amino acid corresponding to the position which recognizes the amino acid or the AMP complex of the amino acid (aminoacylated AMP and aminoacylated AMP analogues and the like) in the tertiary structure of the aminoacyl-tRNA synthetase.

As the amino acid replacement newly introduced into the tyrosyl-tRNA synthetase, in consideration of hydrophilicity and length for hydrogen bond of the amino acid, for example, in the case such that the binding to the aminoacyl-AMP is not formed at the position, the amino acid can be modified with a hydrophobic amino acid, or the distance can be modulated by altering glutamine to asparagine.

In the above example of the invention, tyrosine at position 37 of the tyrosyl-tRNA synthetase was modified with valine, leucine, isoleucine or alanine, and glutamine at position 195 was modified with alanine, cysteine, serine or asparagine, but the modification is not limited thereto.

The method for producing the variant of tyrosyl-tRNA synthetase of the invention wherein the amino acids at the certain positions are modified with the other amino acids is preferably carried out by gene engineering technology known in the art. For instance, the variant enzymes can be simply produced by amplifying DNA modified with the nucleotide sequence encoding the amino acid to be modified using the primers having the modified nucleotide sequence encoding the position of the target amino acid to be modified, subsequently by combining the amplified DNA fragments to obtain expression vector encoding the variant of aminoacyl-tRNA synthetase in full length, and by expressing the enzyme using host cells such as E. coli. The primers used in this method are from about 20 to 70 bases, and preferably from about 20 to 50 bases. It is preferable to use the relatively long primers, for example those of 20 or more bases because this primer has 1 to 3 base mismatches with the original base sequence before the modification.

Also, the method for producing the variants of the tyrosyl-tRNA synthetase of the invention wherein the amino acids at the certain positions are modified with other amino acids is not limited to the method described above, and can use various gene engineering technologies such as point mutation technology and methods where the modified fragment is introduced by restriction enzymes known in the art.

The invention provides cells transformed using the DNA encoding the variant of tyrosyl-tRNA synthetase described above. Such cells may be either prokaryotic or eukaryotic cells.

Also, when the variant of tyrosyl-tRNA synthetase of the invention expressed in cells is used for protein synthesis in the cells as such, the cells responsible for the purpose can be used.

The methods known in the art can be employed as the method for the transformation.

The invention provides the method for producing the proteins containing the unnatural tyrosine analogues substituted at position 3 using the variants of tyrosyl-tRNA synthetase of the invention having the modified amino acid sequences described above. As described above, since the variant of the invention attaches specifically to the unnatural amino acid with 10 folds or more of selectivity, the protein where the target unnatural amino acid is introduced in place of the natural amino acid can be produced by introducing this variant or the gene encoding this variant into the cells followed by the expression thereof.

Also, the variants of tyrosyl-tRNA synthetase of the invention having the modified amino acid sequences include not only the use in the cell but also the use in vitro (cell-free system).

Therefore, the invention provides the method for producing the alloproteins efficiently, selectively, in particular site-selectively and in large amounts.

EXAMPLES

The present invention is more specifically illustrated below by examples, but it is not limited to these examples at all.

Example 1

Preparation of an Expression Vector for TyrRS Gene

A gene of tyrosyl-tRNA synthetase (TyrRS) was cloned from wild-type E. coli, W3110. Next, a plasmid pETYRS was made by inserting the TyrRS gene into pET26b which is a vector of E. coli.

Using this plasmid containing the TyrRS gene of E. coli as the template, a fragment amplified by PCR using the primer (1) and (2) having the following base sequences:

```
Primer (1):                         (SEQ ID NO: 2)
5'-GGAATTCCATATGGCAAGCAGTAACTTGATTAAACAATTGC
AAG-3'

Primer (2):                         (SEQ ID NO: 3)
5'-GCCGAAGCTTGTCGACTTTCCAGCAAATCAGACAGTAATTCT
TTTTACCG-3'
``` was cleaved with NdeI and HindIII, and subsequently ligated at the NdeI-HindIII site of the vector pET26b to make the expression vector of TyrRS, pET-YRS.

Example 2

Determination of Positions where The Mutations are Introduced

Since TyrRS is highly conserved in biological species, using the three dimensional structure of TyrRS and tyrosyl-AMP complex in *Bacillus stearothermophilus* already reported (Brick et al., J. Mol. Bio., 208;83-, 1988), the residues 37 and 195 were found where the mutations should be introduced to incorporate the tyrosine analogues substituted at position 3.

Example 3

Introduction of Site-Specific Mutations

Oligonucleotides including amino acid substitution to be modified were synthesized as respective primers (mutation introducing primers), (3) to (8) by the standard method.

(a) Generation of a Single Amino Acid Substitution Where One Amino Acid was Replaced The DNA sequence encoding the single amino acid substitution where one amino acid at position 37 or 195 was replaced was generated using the primers (3) to (8) shown below. The primers (3) and (4) are for the modification at position 37. And the primers (5) to (8) are for the modification at position 195.

```
Primer (3):                         (SEQ ID NO: 4)
5'-AGGATCGAAGCCGCAAGCGAGCGCGATCGGGCCTTGCGCC-3'

Primer (4):                         (SEQ ID NO: 5)
5'-AGGATCGAAGCCGCAMNNGAGCGCGATCGGGCCTTGCGCC-3'
M denots C or A, and
N denotes A,C,G or T.
```

```
Primer (5):  5'-ACGGTGTGGTGCTGTCTATTGGTGGTTCTGACC-3'    (SEQ ID NO: 6)

Primer (6):  5'-ACGGTGTGGTGCTGGCAATTGGTGGTTCTGACC-3'    (SEQ ID NO: 7)

Primer (7):  5'-ACGGTGTGGTGCTGAACATTGGTGGTTCTGACC-3'    (SEQ ID NO: 8)

Primer (8):  5'-ACGGTGTGGTGCTGTGCATTGGTGGTTCTGACC-3'    (SEQ ID NO: 9)
```

(a) Generation of a double amino acid substitution where two amino acids were replaced The DNA sequence encoding the double amino acid substitution was generated from the plasmids encoding respective single amino acid substitutions at position 37 and 195 by an overlap extension method using the primers, and introduced into the NdeI-BamHI site of pET-YRS. The overlap extension method was performed by purifying two fragments amplified using a pair of the primers (1) and (10) and a pair of the primers (9) and (11), and by amplifying by PCR using the primers (1) and (9) therewith.

```
Primer (1):                                             (SEQ ID NO: 2)
5'-GGAATTCCATATGGCAAGCAGTAACTTGATTAAACAATT
GCAAG-3'

Primer (10):                                            (SEQ ID NO: 11)
5'-GATCATCTGGTTAACGGAGAAGTGTTTGCC-3'

Primer (9):                                             (SEQ ID NO: 10)
5'-TTCTTCGGATCCAACCAGACTGCGCCGCCTTC-3'

Primer (11):                                            (SEQ ID NO: 12)
5'-GACCTTCCTGCGCGATATTGGCAAAC-3'
```

Example 4

Expression of Wild-Type and Variant-Type TyrRS

Each completely mutated DNA fragment obtained from the above process was inserted into an original position of the plasmid pETYRS. *E. coli* BLR(DE3). was transformed with the plasmid containing the wild-type or a variant TyrRS gene by the transformation according to Hanahan's method (J. Mol. Bio., 166:557-580).

Transformants having respective plasmids were isolated, and then cultured in LB medium at 37° C. for 16 hours. The wild-type and variants TyrRS proteins were purified from crude extracts of *E. coli* as described below. All processes were performed at 4° C.

The extract was applied on Ni-agarose column (0.5 mL) equilibrated with buffer A (50 mM Tris-10 mM Mg(OAc)$_2$, pH 7.9, 0.3 M NaCl, 5 mM mercaptoethanol) containing 10 mM imidazole. The column was washed with the buffer A containing 40 mM imidazole and eluted with the buffer A containing 250 mM imidazole. Fractions with the activity were pooled, dialyzed against buffer B (100 mM Tris-HCl, pH 7.6, 40 mM KCl, 10 mM MgCl$_2$, 1 mM DTT), and then glycerol was added at a final concentration of 50% thereto, which was then stored at −20° C.

In the above process, the enzyme variants were obtained which were produced by the substitution at position Tyr 37 with the amino acid selected from the group consisting of alanine, valine, isoleucine and leucine, and the substitution at position Gln 195 with the amino acid selected from the group consisting of serine, cysteine, asparagine and alanine.

Hereinafter, these are referred to as 37A, 37V, 37I, 37L, 195S, 195C, 195N, and 195A, respectively. Additionally, the enzymes with double mutations were obtained which were produced by the substitutions both at positions Tyr 37 and Gln 195. Hereinafter, these are referred to as AS, VS, IS, LS, AC, VC, IC, LC, AN, VN, IN, LN, AA, VA, IA and LA, respectively. These are collectively shown in Table 1.

All enzymes used for gene engineering were purchased from Takara, Toyobo and New England Biolabs (MA, USA). The conditions for gene engineering were determined according to advices from the supplier of the enzyme.

Example 5

Substrate Specificity Assay

In order to evaluate the substrate specificity of these enzyme variants, the following three types of assay methods were used.

The method where the aminoacylation reaction is measured by quantifying inorganic phosphate produced by pyrophosphatase-drived hydrolysis of pyrophosphate which is one of reaction products of the aminoacylation has been described by Lloyd et al. (Nucleic Acids Research, 23:2886-2892, 1995). In one method of the invention, this method was simplified and the aminoacylation reaction was measured by the detection of inorganic phosphate using Biomol green (Funakoshi). Each enzyme obtained was incubated with 0.05 ml of the buffer B containing 1 mM ATP (Seikagaku Corporation), 30 μM purified crude tyrosyl-tRNA, and 100 μM tyrosine or 0.5 mM 3-iodotyrosine at 37° C. for one hour. To stop the reaction, 0.1 ml of Bio mol green was added. Absorbance of its supernatant was measured at 630 nm. The results are shown in Tables 2 and 3.

Table 2 shows the aminoacylation activity of the wild-type enzyme and eight enzymes with a single amino acid mutation by the symbol. Table 3 shows the aminoacylation activity of the wild-type enzyme, 37V, and 16 enzymes with double mutations by the same symbol. It is shown that the activity is high in the order of *>>*>—in each Table.

The enzyme variants obtained by the substitution at positions Tyr 37 and Gln 195 with the other amino acids substantially increased the aminoacylation activity for the tyrosine analogue substituted at position 3. At the same time, relatively, the tyrosylation activity of these proteins is decreased. Therefore, the relative ratios of tyrosine analogue to tyrosine of the enzyme variants are higher than that of the wild-type enzyme.

In the second method, the activity was assayed by Lloyd's method (Nucleic Acids Research, 23:2886-2892, 1995). Each enzyme obtained was incubated with 0.4 ml of the buffer B containing 1 mM ATP (Seikagaku Corporation), 100 μM purified crude tyrosyl-tRNA, 200 μM tyrosine or 3-iodotyrosine at 37° C. for 6 min. The aminoacylation activity was represented as concentrations of released phosphate per min. The result is shown in Table 4.

Table 4 shows the aminoacylation activity of the enzymes with double mutations. Four enzymes with double mutations combine advantages of both mutations at positions Tyr 37 and Gln 195. For instance, the relative ratio of tyrosine analogue to tyrosine of VC is more than 10, and the ratio is higher due to the further mutation at position Gln 195 than that of 37V, the enzyme with a single mutation. VN, VS, and AC are inferior to VC in the relative ratio of tyrosine analogue to tyrosine, but have the higher relative ratio of tyrosine analogue to tyrosine than the substitutions with a single amino acid.

From the result shown in Table 4, it can be concluded that the combination of the mutations at position 37 and 195 could dramatically alter the substrate specificity of the enzyme and increase the aminoacylation activity for the tyrosine analogue substituted at position 3. Among the enzyme variants, VC, VN and AC have the most remarkable property and applicability.

In the third method, the aminoacylation activity for tyrosine or 3-iodotyrosine for tRNA in full length was assayed by the same method as acidic polyacrylamide electrophoresis by the method of Wolfson et al. (Wolfson, A. D. et al., RNA, 4:1019-1023, 1998). Tyrosine or iodotyrosine at 200 μM and the enzyme at 50 nM were incubated at 37° C. for 3 min, and subsequently the electrophoresis was carried out. The result of the aminoacylation activity of the enzymes with double mutations are shown on the photo, substitute for a drawing, in FIG. 1. In FIG. 1, left three lanes are from the wild-type enzyme, middle three lanes are from the enzyme modified at position 37 with valine (37V) and right three lanes are from the enzyme modified at positions 37 and 195 with valine and cysteine (VC), respectively. Three lanes in each group show the case without the addition of the amino acid (w/o aa), the case with the addition of 3-iodotyrosine (200 μM) (1-Tyr), and the case with the addition of tyrosine (200 μM) (Tyr), respectively from the left.

As a result, it was found that VC had high specificity for the tyrosine analogue.

Example 6

Production of Protein with Site-Specific Insertion of Unnatural Amino Acids

The protein containing iodotyrosine was generated by the reaction according to a batch method in a wheat germ cell-free protein synthesis system using the resultant variant with double mutations, VC and the amber suppressor tRNA derived from tyrosine tRNA of *E. coli*.

Cell-free protein synthesis in the wheat germ system was carried out using Proteios cell-free protein synthesis kit (Toyobo). A target protein is a short chain type of c-H-Ras added His tag at its C-terminus via a spacer sequence (Milburn et at., Science 247:939-945, 1990). A plasmid used for the expression of the protein was made by inserting a gene corresponding to a sequence where a thrombin recognition sequence and His tag were added to the C-terminus of the short chain type of c-H-Ras at SpeI-SalI site of a plasmid, pEU3-NII attached in the kit. When the amino acid sequence of the translation product consequently predicted is represented by the single character code for amino acids, it is as follows (SEQ ID NO: 13).

| | |
|---|---|
| MTEYKLVVVGAGGVGKSALTIQLIQNHFVD | 30 |
| EYDPTIEDSYRKQVVIDGETCLLDILDTAG | 60 |
| QEEYSAMRDQYMRTGEGFLCVFAINNTKSF | 90 |
| EDIHQYREQIKRVKDSDDVPMVLVGNKCDL | 120 |
| AARTVESRQAQDLARSYGIPYIETSAKTRG | 150 |
| GVEDAFYTLVREIRQHKLRKLGSLVPRGSH | 180 |
| HHHHH | 185 |

The translation reaction was carried out by further adding iodotyrosine at a final concentration of 0.6 mM in addition to the condition of the kit. The product was electrophoresed using 4-12% NuPAGE Bis-Tris gel (Invitrogen). Using an image analyzer FLA-2000 (Fujifilm, Tokyo, Japan), counts of RI of bands on the gel were quantified, or protein bands stained using Cypro-tangerine protein gel stain (Molecular probes) on the gel were quantified.

In the translation using mRNA made from a construct where the 32nd codon of this protein was replaced by the amber codon as the template, the production of the protein in full length was dependent on coexistence of both TyrRS and the suppressor tRNA (FIG. 2). This proves that the suppressor tRNA used is scarcely aminoacylated by the endogenous aminoacyl-tRNA synthetase in the wheat germ. The synthesized quantity by the amber suppression was 30 to 40% of the control with no amber codon. In order to increase the synthesized quantity of the protein, the reaction by the suppression was carried out for 3 days using a dialysis method. In this case, it was found that a quantity of the production was 0.1 mg or more in terms of the quantity per ml of reaction solution and that the protein could be synthesized sufficiently in quantity to perform various experiments using proteins.

Example 7

Mass Spectrometric Analysis of the Products in Cell-Free Protein Synthesis

It was examined by mass spectrometric analysis that iodotyrosine was actually inserted at the position corresponding to the amber codon of the peptide chain. The synthesized protein was purified using Ni-NTA magnetic agarose beads (Qiagen) for LC-MS analysis. The purified protein was further purified by electrophoresis using NuPAGE Bis Tris gel, and a band of 21 kDa corresponding to the target product was cut out from the gel. Digestion using 0.1 μg of Achromobacter protease I (Lys-C) was carried out in 0.05 M of Tris-HCl (pH 9) containing 0.1% SDS in a gel fragment at 37° C. for 12 hours. Peptides produced by the digestion were separated using model 1100 liquid chromatography (Hewlett Packard) connecting DEAE-5PW (1×10 mm, Tosoh, Tokyo) and Mightysil C18 (1×50 mm, Kanto Chemical, Tokyo) by solvent B with a linear gradient of 2 to 60% over 30 min. The detection was carried out by a diode-array detector. Solvents A and B were an aqueous solution of 0.09% (v/v) trifluoroacetate and 0.075% (v/v) trifluoroacetate-80% (v/v) acetonitrile, respectively. Elutes were analyzed by Finnigan LCQ ion trap mass spectrometer using ESI probe. Tandem MS sequencing was carried out for the fragment corresponding to $[M+2H]^{2+}$ of Lys-C fragment containing the 32nd amino acid of Ras.

Figure 3:
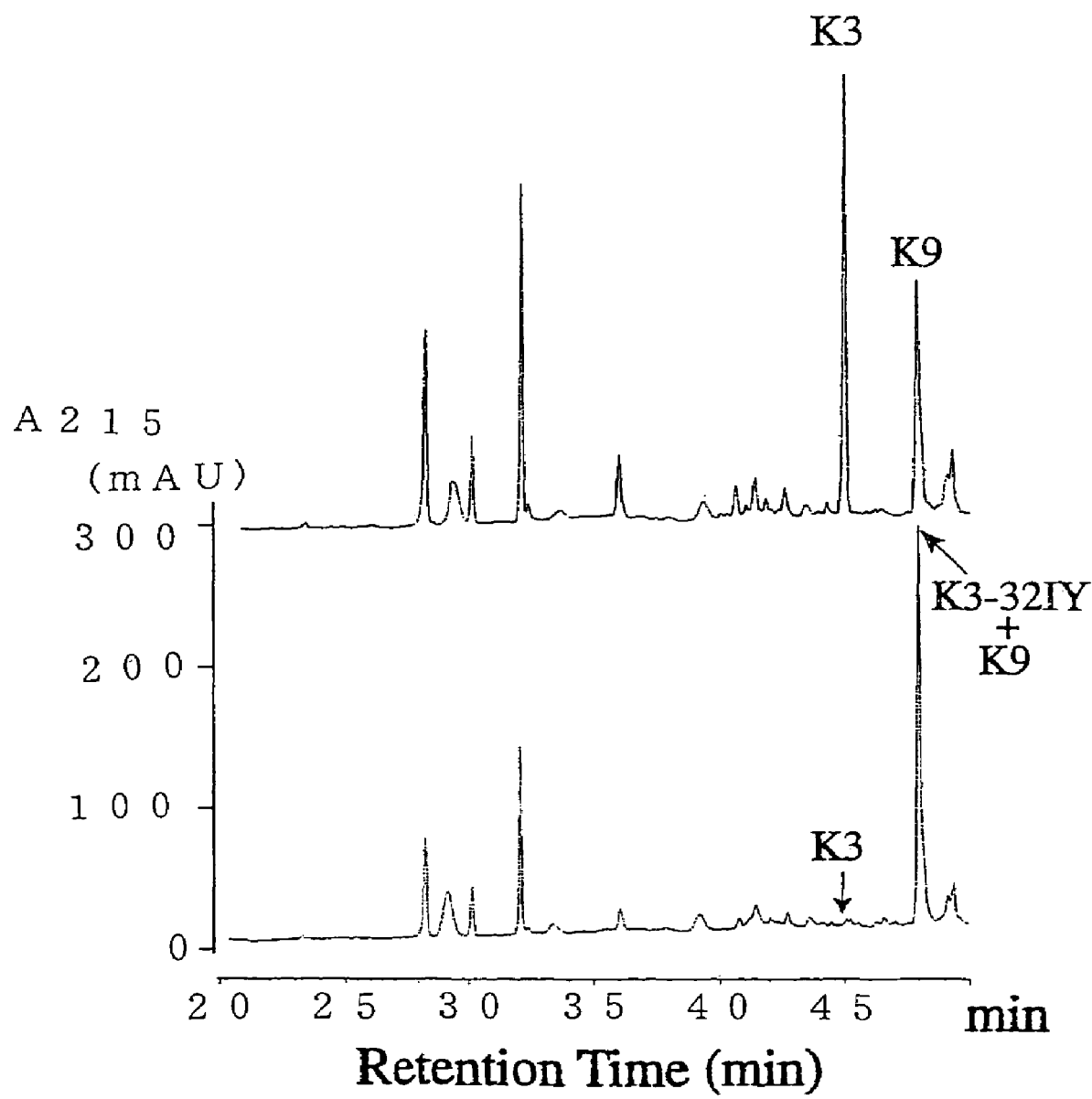
FIG. 3 shows charts of liquid chromatography in LC-MS analysis of translation products in the wheat germ cell-free translation system in which iodotyrosine, TyrRS-VC variant specific for iodotyrosine and the suppressor tRNA were included.

Among the fragments obtained by digesting the translation products, the fragment containing the 32nd amino acid from the N-terminus (Ser 17 to Lys 42, referred to as K3 fragment) was focused and analyzed. As a result, the majority of the K3 fragments produced by the amber suppression had the mass corresponding one where one residue of tyrosine was replaced by iodotyrosine, and only minor fragments had the mass not including iodotyrosine. No K3 fragment was detected where the other amino acid was accidentally inserted at the site corresponding to the amber codon. The ratio of iodotyrosine to tyrosine inserted to the amber codon was examined by absorbance of chromatogram. Consequently, it was found that 95% or more of K3 fragments encompassed iodotyrosine by the amber suppression whereas the ratio of tyrosine insertion at the amber codon was 5% or less. On the other hand, no fragment having the mass corresponding to the case encompassing iodotyrosine in place of tyrosine was detected in the analysis of the translation products from mRNA which did not contain the amber codon. This confirmed that the canonical codon for tyrosine was not contaminated with iodotyrosine (FIG. 3).

Additionally, Phe-Val-Asp-Glu-(iodo-Tyr)-Asp (SEQ ID NO: 14) which is a partial sequence of this fragment was confirmed by the tandem mass analysis of the K3 fragment containing iodotyrosine.

Industrial Applicability

The present invention provides novel variants of tyrosyl-tRNA synthetase and novel methods for the modification. According to the method for the modification of the invention, the modifications of selectivity and substrate specificity of tyrosyl-tRNA synthetase can be efficiently carried out by the simple method.

The use of the variant of tyrosyl-tRNA synthetase of the invention enables site-specific insertion of tyrosine analogue substituted at position 3, in addition to natural amino acids, by utilizing aminoacylation reaction upon the preparation of peptide or protein.

Also, the use of the variant of tyrosyl-tRNA synthetase of the invention makes it possible to produce alloproteins suitable for mass production efficiently and selectively.

The invention claimed is:

1. An isolated tyrosyl-tRNA synthetase consisting of the amino acid sequence of SEQ ID NO: 1, with the exception that the tyrosine at position 37 and the glutamine at position 195 are substituted, such that said tyrosyl-tRNA synthetase incorporates one or more unnatural tyrosine analogues substituted at position 3 more efficiently than natural tyrosine.

2. The tyrosyl-tRNA synthetase according to claim 1, wherein the tyrosine at position 37 and the glutamine at position 195 of the tyrosyl-tRNA synthetase consisting of the amino acid sequence of SEQ ID NO:1 are substituted with valine, leucine, isoleucine or alanine, and alanine, cysteine, serine or asparagine, respectively.

* * * * *